United States Patent
Guy

(10) Patent No.: US 9,839,499 B2
(45) Date of Patent: *Dec. 12, 2017

(54) DENTAL DEVICES

(76) Inventor: Frederick R. Guy, Syracuse, NY (US)

(*) Notice: Subject to any disclaimer, the term of this patent is extended or adjusted under 35 U.S.C. 154(b) by 319 days.

This patent is subject to a terminal disclaimer.

(21) Appl. No.: 13/295,248

(22) Filed: Nov. 14, 2011

(65) Prior Publication Data

US 2013/0224684 A1 Aug. 29, 2013

Related U.S. Application Data

(60) Provisional application No. 61/413,061, filed on Nov. 12, 2010.

(51) Int. Cl.
| | | |
|---|---|---|
| *A61C 13/08* | (2006.01) | |
| *A61C 13/00* | (2006.01) | |
| *A61L 27/54* | (2006.01) | |
| *A61C 8/00* | (2006.01) | |
| *A61C 13/01* | (2006.01) | |
| *A61K 6/033* | (2006.01) | |
| *A61C 5/77* | (2017.01) | |

(52) U.S. Cl.
CPC ............... *A61C 13/08* (2013.01); *A61C 5/77* (2017.02); *A61C 8/00* (2013.01); *A61C 13/0004* (2013.01); *A61C 13/0006* (2013.01); *A61C 13/0022* (2013.01); *A61C 13/01* (2013.01); *A61K 6/033* (2013.01); *A61L 27/54* (2013.01); *A61L 2300/30* (2013.01)

(58) Field of Classification Search
CPC .. A61C 13/08; A61C 5/77; A61C 8/00; A61C 13/0004; A61C 13/0006; A61C 13/0022; A61C 13/01; A61K 6/033; A61L 27/54; A61L 2300/30

USPC ....... 433/172–176, 201.1, 202.1, 199.1, 215, 433/223; 241/15

See application file for complete search history.

(56) References Cited

U.S. PATENT DOCUMENTS

| | | | |
|---|---|---|---|
| 4,693,986 A * | 9/1987 | Vit et al. .......................... 501/1 |
| 4,937,928 A | 7/1990 | van der Zel | |
| 5,378,154 A | 1/1995 | Van Der Zel | |
| 7,708,557 B2 * | 5/2010 | Rubbert ........................ 433/173 |
| 2006/0210494 A1 * | 9/2006 | Rabiei et al. ................... 424/57 |

FOREIGN PATENT DOCUMENTS

| | | |
|---|---|---|
| KR | 1020060054668 | 5/2006 |
| KR | 1020110056594 | 5/2011 |

OTHER PUBLICATIONS

Hunger, Fred J., Tagua: The Vegetable Ivory Substitute, from Fine Woodworking magazine (Jul. 1990), p. 49, retreived from http://books.google.com/books?id=eI30loPhRdcC&pg=PA49&lpg=PA49&dq=tagua+dentures&source=bl&ots=RywvCNpCs6&sig=BJ_iB1fLhR5hFkny9yolFnwGamQ&hl=en&sa=X&ei=1JhlUrWiMszc4AOa34CIAQ&ved=0CE0Q6AEwAQ#v=onepage&q=tagua%20dentures&f=true.*

Vegetable Ivory retreived from http://waynesword.palomar.edu/pljan99.htm on Mar. 21, 2014.*

(Continued)

*Primary Examiner* — Heidi M Eide
(74) *Attorney, Agent, or Firm* — Medley, Behrens & Lewis, LLC

(57) ABSTRACT

The present invention is a dental device comprising natural and sustainable materials. These materials are derived from the nut of the tangua palm tree that may be fashioned into devices for human and animals when replacing one or more teeth of the subject.

1 Claim, 4 Drawing Sheets

(56) References Cited

OTHER PUBLICATIONS

Denture. (n.d.). Dictionary.com Unabridged. Retrieved Mar. 21, 2014, from Dictionary.com website: http://dictionary.reference.com/browse/denture.*

Blog about history of dentures retreived from http://drnealblog.blogspot.com/2011/09/interesting-facts-in-history-of.html on Mar. 21, 2014.*

PCT International Search Authority, International Search Report and Written Opinion, PCT/US2011/060529, dated Jun. 19, 2012 (12 pages).

* cited by examiner

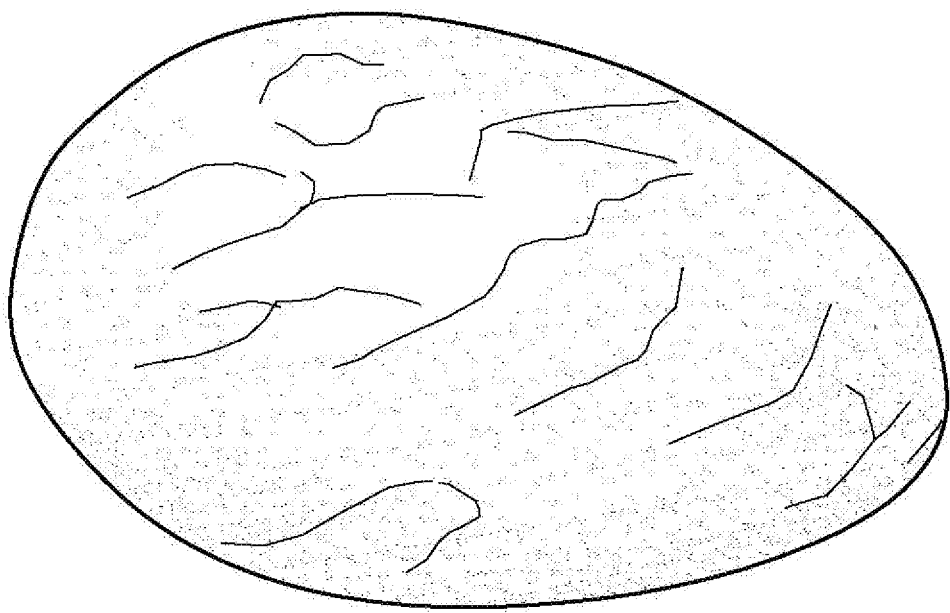
Figure 1
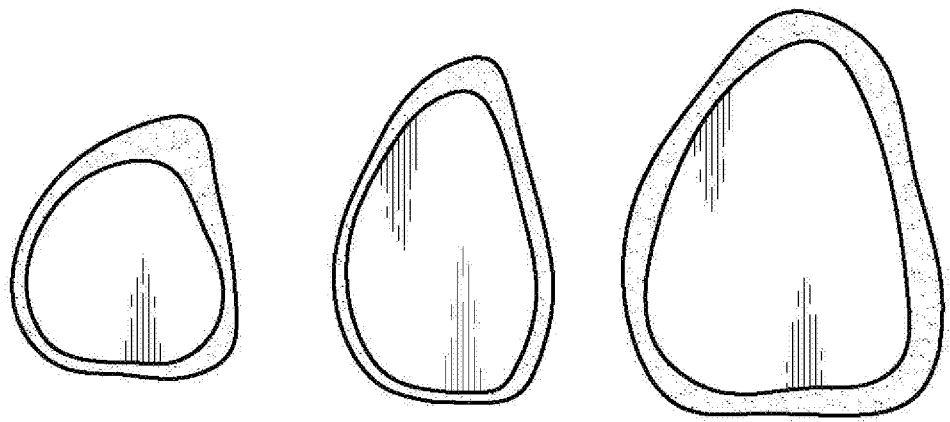
Figure 2
Hydroxylapatite
$$Ca_{10}(PO_4)_6(OH)_2$$
Figure 3

DENTAL DEVICES

I claim priority to my provisional application, Ser. No. 61/413,061, filed on Nov. 12, 2010.

SUMMARY OF THE INVENTION

The present invention applies to typical dental devices or appliances having chewing surfaces 100 comprising naturally derived materials obtained from sustainable resources. The natural material has physical characteristics providing durability, texture, color and shading that match natural teeth necessary for utilitarian and cosmetically pleasing dental devices. The natural materials are sufficiently workable when using normal manufacturing techniques and equipment routinely applied for making currently available dental devices comprising non-natural or sustainable materials such as metal and ceramics.

BACKGROUND OF THE INVENTION

Animals, particularly humans have natural teeth to assist in mastication of food and are essential for sustaining good health. Teeth, however, comprise living tissue that may be corruptible by neglect, abuse and, or disease. In extreme cases decayed or damaged teeth are not reparable with typically available prophylaxis and must be extracted for the well being of the patient. Notwithstanding removal, in the opinion of dental professionals, it is important that extracted teeth be replaced by prosthesis equipped with chewing surfaces. Replacements for teeth and the method for making such replacements are well known to those skilled in the art and include devices selected from the group consisting of bridges, full dentures, partial dentures, crowns, caps and combinations thereof.

The aforementioned dental devices are currently made from a number of materials that provide sufficient durability to sustain the rigors of chewing as well as provide good cosmetic aesthetics to match the remaining natural teeth in terms of physical factors including, but not necessarily limited to shape, size, texture and color. Currently the materials used to make such devices include non-sustainable precious metals such as gold, ceramics, porcelain, plastics or composites of these materials. Standard dental devices are typically made of the above materials with a uniform high degree of hardness throughout the material. Unlike natural teeth which consist of multiple layers of organic and mineral material in an ascending degree of hardness, from root to dentin to enamel, which has both formal and functional qualities and characteristics. Those qualities and characteristics are perfectly adapted to provide a kind of cushion or shock absorbing effect which protects the surrounding maxillofacial structure from stress induced damage. Such damage can include serious bone, muscular, and nerve damage, which is more likely to occur when superfluously hard and rigid dental prosthetics, replace natural teeth which have a shock absorbing quality.

The present invention provides a natural, agriculturally derived solution that has substantially the same variable component hardness, and cushioning effect, as natural teeth.

Most dentists and dental patients have expressed high interest in prosthetic dental devices comprising natural, sustainable or "green" materials. Up to now, however no suitable natural and sustainable materials has been found to be a satisfactory in terms of the physical attributes previously mentioned. Therefore, there remains an unmet need for dental devices comprising a natural, sustainable material.

BRIEF DESCRIPTION OF THE SEVERAL DRAWINGS

FIG. 1 is a perspective view of an example Tagua Nut.

FIG. 2 is a cross-sectional view of examples of a Tagua Nut Endosperm.

FIG. 3 is the chemical formula for hydroxylapatite.

DETAILED DESCRIPTION OF THE INVENTION

A. The Dental Device Material

Figure 4:
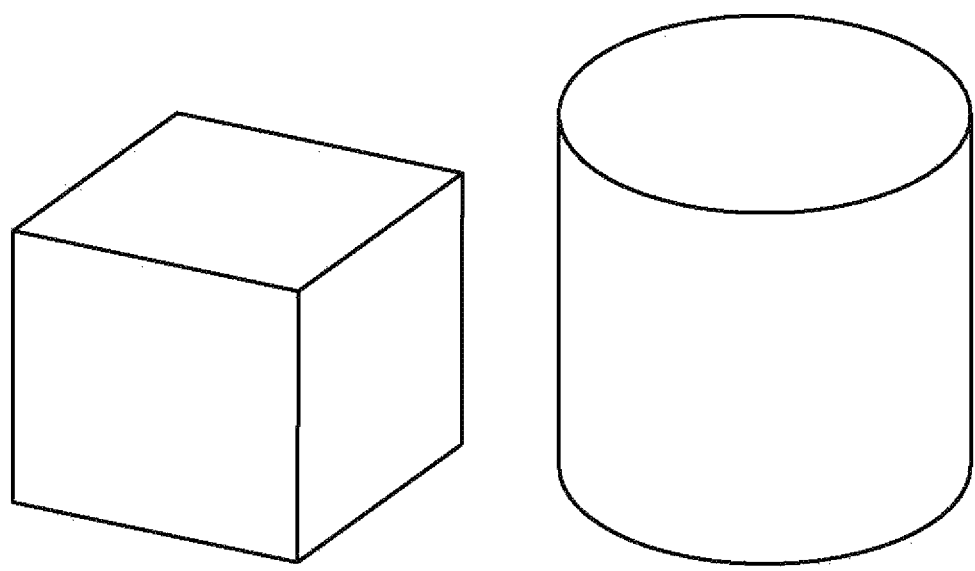
FIG. 4 is a perspective view of examples of carved Tagua shapes.

In an embodiment of the invention, the dental devices comprise dehydrated and hardened endosperm of the nut of the Tagua palm, a species of the genus *Phytelephas* [FIG. 1]. *Phytelephas* is a genus containing six species of palms (family Arecaceae), occurring from southern Panama along the Andes to Ecuador, Bolivia and Peru. They are medium-sized to tall palms reaching 20 meters tall, with pinnate leaves. They are commonly known as ivory palms, ivory-nut palms or Tagua palms; their scientific name means "plant elephant". This and the first two of the common names refer to the very hard white endosperm of their seeds (Tagua nuts), which resembles elephant ivory. In its original state, the "nut" is covered with pericarp. The nut is covered with a brown, flaky skin and shaped like a small avocado, roughly 4-8 cm in diameter. Since the nut has a protective husk or shell, once the nuts are harvested there are no extreme inspection, sorting and handling that must be taken to sort the nuts before processing. This material is harvested by the usual manual or machine harvesting methods generally known in the art.

The dehydrated Tagua nut material's texture, color and shading vary over the range normally associated with natural teeth. To that end, the desired shading and color of the material is selected individually for the patient prior to manufacturing the device. Furthermore, the color of the material can be modified by routine method known in the art for bleaching material or foods such as wheat flour. Additionally the texture of the material may be manipulated to create a consistent surface of the device that matches the natural teeth to avoid preoccupation by the patient's tongue.

B. Processing the Dental Device Material

Processing the dental device material derived from the Tagua nuts includes the steps of shelling, and curing the nuts by dehydration or desiccation. Dehydration or desiccation may be achieved wherein the nuts are dried at ambient conditions or accelerated using industrial equipment to rapidly drive off water to a desired level of dryness. Such equipment is well known in the foods industry. The point whereupon the nuts are sufficiently dehydrated for manufacturing dental devices is at the point of comparable hardness of the natural dentin part of a tooth. Standard testing equipment to makes such measurements includes an Instron® Device. This device may be set to measure compressive strength in Pascals that is defined as the value of uniaxial compressive stress necessary to achieve complete failure of the material. Other methods of testing hardness include the Mohs Hardness method. The Mohs Scale of mineral hardness characterizes the scratch resistance of various minerals through the ability of a harder material to scratch a softer material. The Mohs Hardness of dehydrated Tagua is roughly the equivalent to the Mohs Hardness of natural tooth dentin, ranging between 2.5 and 4 on the Mohs Hardness scale. Upon reaching compressive strength comparable to the primary dentin subsurface part of a natural tooth, the nut meat [FIG. 2] is processed and shaped into blocks, or other shapes [FIG. 3], that are of certain standard dimensions that are equivalent to those of the standard artificial material currently used in the computer aided design or CAD and manufacturing of dental prostheses.

Among the systems known to those skilled in the art of dental device manufacturing is the Chairside Economical Restoration of Esthetic Ceramics™ Series including the CEREC™ AC dental milling device. Such milling devices carve blocks of ceramic, composite, or other suitably hard material that are made in such dimensions as to fit in the milling compartment of the machine. The milling device fashions a product of certain size and quality based upon a computer generated 3 dimensional rendering of a particular patient's data. The dehydrated Tagua nut endosperm is preliminarily shaped according to the requirements for use in the CEREC device, or any other brand of milling device, in such a way that a uniform and consistently solid piece in the desired shape and dimensions is produced without any of the naturally occurring gaps or crevices found in the nut. The pieces of Tagua may at this stage of production be treated in one of several ways with the mineral hydroxylapatite [FIG. 3] which is a naturally occurring mineral which is a primary element in human teeth and bone. One method of treating the dehydrated Tagua endosperm is to bath the Tagua within a solution of hydroxylapatite under such conditions that achieves a suitable coating and desired hardening of the surface. Hydroxylapatite, also called hydroxyapatite (HA), is a naturally occurring mineral form of calcium apatite with the formula $Ca_5(PO_4)_3(OH)$, but is usually written $Ca_{10}(PO_4)_6(OH)_2$ to denote that the crystal unit cell comprises two entities. Hydroxylapatite is the hydroxyl end member of the complex apatite group. The $OH^-$ ion can be replaced by fluoride, chloride or carbonate, producing fluorapatite or chlorapatite. It crystallizes in the hexagonal crystal system. Pure hydroxylapatite powder is white. Naturally occurring apatites can, however, also have brown, yellow, or green colorations, comparable to the discolorations of dental fluorosis. Alternative coating methods can be used that involve adhesion or admixture of the Tagua endosperm with the hydroxylapatite. A thermal or plasma surface treatment method may be used for example. Moreover the treatment may also be made, or repeated, after the final dental prosthetic has been carved. Such treatment is used when additional hardness or other qualities that result from the treatment are desired.

Pulverization of dehydrated Tagua provides for later reconstitution of the material in various admixtures with hydroxyapatite such that desired qualities of size, shape, and hardness may be achieved [FIG. 4]. Various standard chemical treatments can be applied to adjust qualities of size, color, and hardness.

Figure 5:
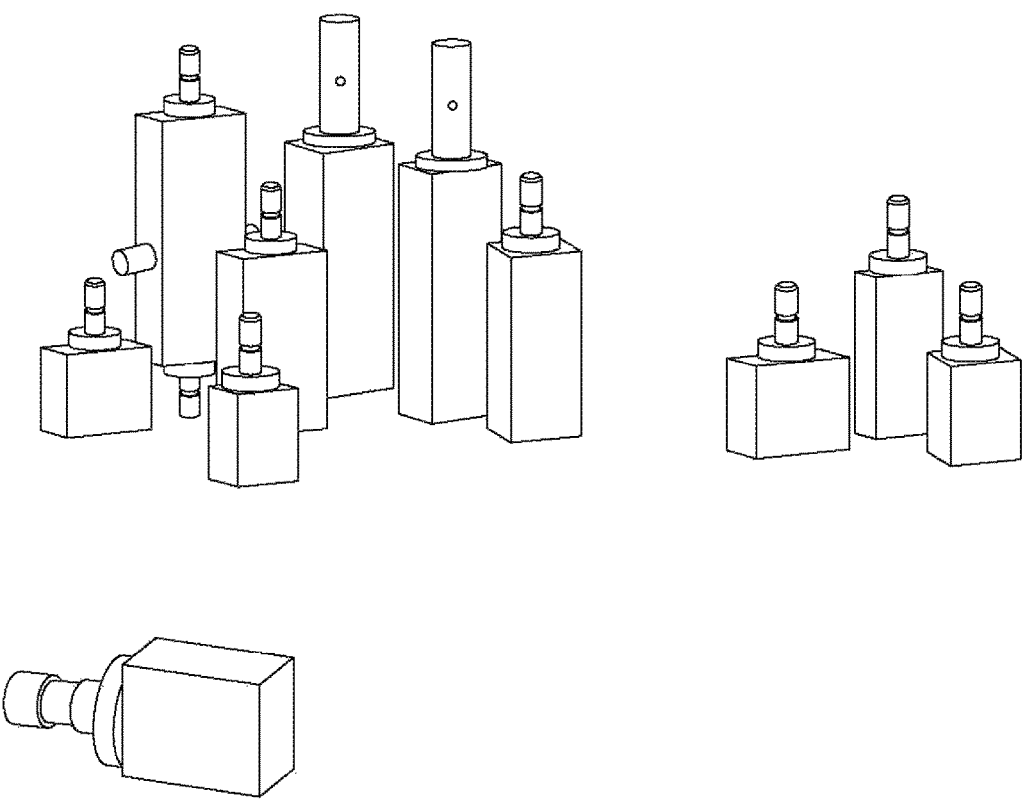
FIG. 5 is a perspective view of examples of final tagua shaped pieces ready for milling.
Figure 6:
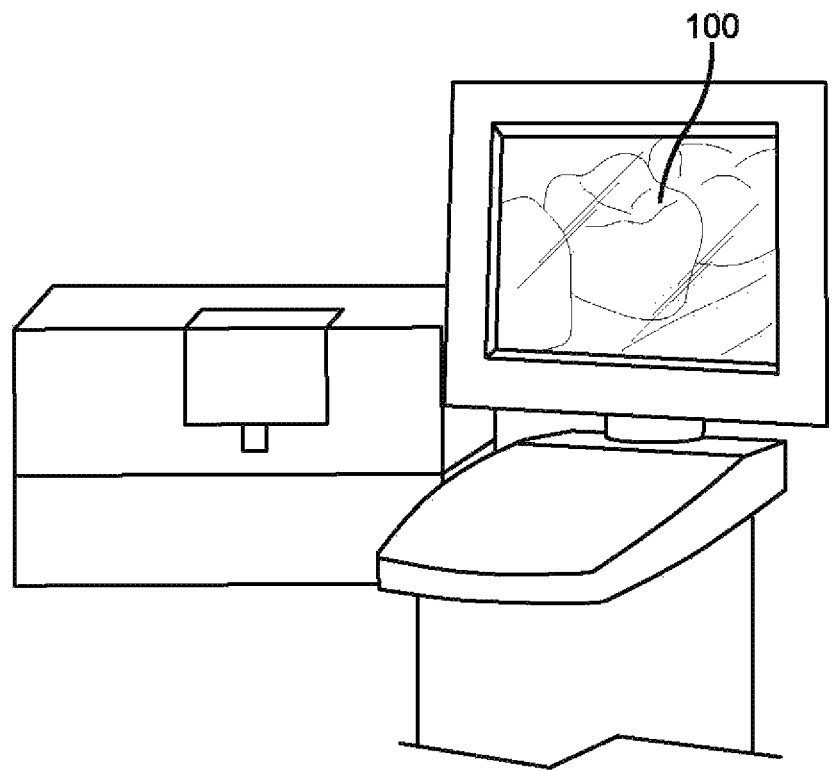
FIG. 6 is a perspective view of an example CAD/CAM "CEREC" Dental Milling Device.

Before placing the dehydrated Tagua nut endosperm into the CEREC or other milling device, a standard abutment or stem may be attached to the piece so that it can be held and manipulated by the device during the milling step. [FIG. 5]. Then the appropriately sized and shaped piece that is suitable to produce the desired prosthetic for given patient is carved in accordance with the computer assisted design data related to the patient using the milling device [FIG. 6], so as to be capable of attachment to a dental implant.

Figure 7:
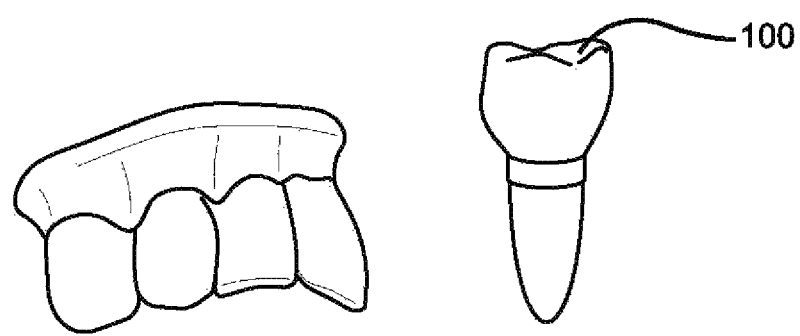
FIG. 7 is a perspective view of examples of finished dental prostheses.

The resulting prosthetic [FIG. 7] is then attachable to a patient's standard implant which may be of any type. Alternatively, the prosthetic can be fitted to cap a broken tooth by mounting upon a suitably prepared fractional part of an original remaining tooth or teeth. The resulting prosthesis may be of any type, without limitation to, a cap, crown, bridge, partial, or complete denture set. The prosthetic need not attach permanently to implants, as when comprising a removable denture set or bridge for example.

Because the dehydrated endosperm of the Tagua nut, while sufficiently hard, is not superfluously hard in comparison to natural teeth as are the typical ceramic and composite materials ordinarily used by dental milling devices, the carving bits need changing less frequently. What's more less expensive carving bits may be used in place of the diamond bits otherwise needed.

It is apparent that the sequence of steps involved here may be altered and that other vegetable material of the same genus and species may be substituted for the Tagua nut endosperm without departing from the spirit and scope of the invention. The prostheses contemplated can also be hand carved, using standard power or hand carving tools, both during the fabrication stage and for the purpose of making fitting adjustments.

A sustainable green business is attained by the practice of the methods here that provides a more biocompatible dental prosthesis without any adverse impact on patient health in contrast to the potentially toxic elements, byproducts, and waste related to the manufacturing of other currently used ceramic, composite, artificial products.

The above invention is not necessarily limited in scope and includes discernible variations or modifications obvious to one skilled in the art.

I claim:
1. A dental device comprising a chewing surface:
   the chewing surface comprising a naturally derived material;
   wherein the naturally derived material is derived from a vegetable nut;
   wherein the chewing surface includes a crown chewing surface;
   wherein the naturally derived material is the vegetable nut in a dehydrated or desiccated state;
   wherein the crown chewing surface is sealed by a layer of a naturally occurring mineral.

* * * * *